United States Patent
Aoki

(10) Patent No.: US 7,459,688 B2
(45) Date of Patent: Dec. 2, 2008

(54) RADIATION DETECTION CIRCUIT AND APPARATUS FOR RADIOGRAPHIC EXAMINATION

(75) Inventor: Kenichi Aoki, Higashimurayama (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 114 days.

(21) Appl. No.: 11/518,279

(22) Filed: Sep. 11, 2006

(65) Prior Publication Data
US 2007/0114427 A1    May 24, 2007

(51) Int. Cl.
G01T 1/164    (2006.01)
(52) U.S. Cl. .................................. 250/363.03
(58) Field of Classification Search . 250/363.01–363.1, 250/370.09, 269.3, 269.5, 269.7
See application file for complete search history.

(56) References Cited

U.S. PATENT DOCUMENTS

| 4,531,058 | A | * | 7/1985 | Burnham et al. | 250/363.03 |
| 5,793,045 | A | * | 8/1998 | DiFilippo et al. | 250/363.03 |
| 5,841,140 | A | * | 11/1998 | Mc Croskey et al. | 250/363.03 |
| 5,892,227 | A | * | 4/1999 | Schieber et al. | 250/370.12 |
| 6,374,192 | B1 | | 4/2002 | Brogle et al. | |
| 2004/0195512 | A1 | * | 10/2004 | Crosetto | 250/363.04 |
| 2005/0067571 | A1 | * | 3/2005 | Yanagita et al. | 250/363.03 |
| 2005/0109958 | A1 | | 5/2005 | Vernon | |

FOREIGN PATENT DOCUMENTS

JP    09-127249    5/1997
JP    2003-004853    1/2003
JP    2003-043149    2/2003

OTHER PUBLICATIONS

Lim, Hansang et al., "Comparison of Time Corrections Using Charge Amounts, Peak Values, Slew Rates, and Signal Widths in Leading-Edge Discriminators", Review of Scientific Instruments vol. 74, No. 6, Jun. 2003, pp. 3115-3119.
Preliminary Search Report 06 53666 filed Sep. 11, 2006.
Alan Wintenberg, "Integrated Circuit Front-Ends for Nuclear Pulse Processing: Front-end Circuits for Timing Applications", 2003 IEEE-Nuclear Science Symposium, a total of 10 sheets.

* cited by examiner

Primary Examiner—David P. Porta
Assistant Examiner—Kiho Kim
(74) Attorney, Agent, or Firm—Squire, Sanders & Dempsey L.L.P.

(57) ABSTRACT

An apparatus for radiographic examination includes a detection unit including a detector configured to detect a gamma ray emitted from a radioactive isotope in an object and to output a detected signal, a first measurement unit configured to determine a first crossing time at which a pulse height of the detected signal becomes substantially equal to a first threshold value, a second measurement unit configured to determine a second crossing time at which the pulse height of the detected signal becomes substantially equal to a second threshold value, and an incidence time calculation unit configured to calculate a starting time of the detected signal based on the first crossing time and the second crossing time and to output detection data; and an information processing unit configured to determine distribution of radioactive isotopes in the object based on multiple sets of said detection data.

13 Claims, 13 Drawing Sheets (A)　　　　　(B)

(A)　　　　　(B)

RADIATION DETECTION CIRCUIT AND APPARATUS FOR RADIOGRAPHIC EXAMINATION

BACKGROUND OF THE INVENTION

1. Field of the Invention

The present invention generally relates to a radiation detection circuit and an apparatus for radiographic examination, and more particularly relates to a radiation detection circuit and an apparatus for radiographic examination that detect two gamma rays emitted from a radioactive isotope in the object at the same time.

2. Description of the Related Art

Positron emission tomography apparatuses are being used to obtain detailed information on the object. Before a diagnosis using a PET apparatus, diagnostic agents labeled by positron nuclides are introduced into the object by injection or inhalation. The diagnostic agents introduced into the object accumulate in a body part having a function corresponding to the diagnostic agents. For example, diagnostic agents made of saccharide accumulate preferentially in a part of the object where metabolism is high, for example, cancer cells. The positron nuclide of the diagnostic agent emits a positron. When the emitted positron collides with one of surrounding electrons, both are annihilated and two gamma rays are emitted at approximately 180 degrees to each other. The two gamma rays are detected at the same time by gamma ray detectors surrounding the object and recorded as signals. A computer processes recorded signals and generates image data showing the distribution of radioactive isotopes in the object. While a computer tomography (CT) scanner used for detailed diagnosis provides structural information on a lesion in the object, a PET apparatus provides functional information on the inside of the object and therefore makes it possible to clarify the pathologies of various intractable diseases.

A PET apparatus determines that the signals are valid only when two gamma rays emitted from a positron nuclide at approximately 180 degrees to each other are detected at the same time by a pair of gamma detectors facing to each other across the object. For example, when only one gamma ray is detected at a time, the signal is discarded as invalid. Even when two gamma rays are detected at two close time points, the signals are discarded as invalid if the time difference between the two time points is greater than a specified value. For the above reasons, it is necessary to precisely determine the time at which a gamma ray enters a gamma ray detector.

A gamma ray detection circuit obtains the time (detection point) of a detected signal the pulse height of which detected signal increases in the time axis direction, and uses the detection point as the incidence time of the gamma ray. Various types of detection circuits for determining the detection point of a detected signal have been proposed. For example, a detection circuit uses the time at which a detected signal reaches a specified pulse height as the detection point. An advantage of such a detection circuit is that the circuit configuration is simple. However, obtained detection points may fluctuate depending on the maximum pulse heights of detected signals or depending on the waveforms of detected signals.

In a detection circuit 100 as shown in FIG. 1, a zero-cross comparator 102 compares a signal Yz obtained by dividing the voltage of a detected signal by voltage dividing resistors R1 and R2 with a signal Xz obtained by delaying the detected signal for a specified period of time by a delay circuit 101. The detection circuit 100 then generates an output signal using the zero-crossing time as a detection point. Such a circuit is called a constant fraction discriminator (CFD) (see, for example, non-patent document 1).

A CFD outputs a pulse when a certain period of time passes after a detected signal reaches a certain pulse height, determines the time at which the pulse has been output, and uses the time as a detection point. A CFD can determine a detection point independently of the pulse height itself of a detected signal, thereby reducing the fluctuation of detection points.

[Non-patent document 1] 2003 IEEE-Nuclear Science Symposium, Integrated Circuit Front-Ends for Nuclear Pulse Processing: Short Course "Front-end Circuits for Timing Applications" by Alan Wintenberg However, since the delay circuit 101 of the detection circuit 100 shown in FIG. 1 is normally formed by connecting many operational amplifiers, the configuration of the detection circuit 100 is complicated.

To increase the positional accuracy and efficiency of gamma ray detection in a PET apparatus, it is necessary to miniaturize a detector and thereby to arrange a large number of detectors in the PET apparatus. Increasing the number of detectors makes it necessary to increase the number of detection circuits. Therefore, in practice, it is necessary to form detection circuits on a semiconductor chip. Also, depending on the characteristics of a detector, it may be necessary to adjust the delay time of the delay circuit 101 shown in FIG. 1. However, adjusting the delay time requires changing the number of operational amplifiers and the design of a semiconductor chip, and therefore requires rebuilding the semiconductor chip. This results in increased production costs and increased production time of a PET apparatus. Further, similar problems occur when changing the design of a detector or when using detectors with different characteristics.

SUMMARY OF THE INVENTION

The present invention provides a radiation detection circuit and an apparatus for radiographic examination that substantially obviate one or more problems caused by the limitations and disadvantages of the related art.

Embodiments of the present invention provide a radiation detection circuit having a simple circuit configuration and an apparatus for radiographic examination that can precisely determine the incidence time indicating when a gamma ray has entered a detector.

According to an embodiment of the present invention, an apparatus for radiographic examination includes a detection unit including a detector configured to detect a gamma ray emitted from a radioactive isotope in an object and to output a detected signal, a first measurement unit configured to determine a first crossing time at which a pulse height of the detected signal becomes substantially equal to a first threshold value, a second measurement unit configured to determine a second crossing time at which the pulse height of the detected signal becomes substantially equal to a second threshold value that is greater than the first threshold value, and an incidence time calculation unit configured to calculate a starting time of the detected signal based on the first crossing time and the second crossing time which the starting time indicates when a waveform of the detected signal has started to rise and is used as an incidence time indicating when the gamma ray has entered the detector and to output detection data including. the incidence time; and an information processing unit configured to determine distribution of radioactive isotopes in the object based on multiple sets of said detection data that are valid according to the incidence time.

According to another embodiment of the present invention, a radiation detection circuit for obtaining an incidence time indicating when a gamma ray has entered a detector includes a first measurement circuit configured to determine a first crossing time at which a pulse height of a detected signal output from the detector becomes substantially equal to a first threshold value; a second measurement circuit configured to determine a second crossing time at which the pulse height of the detected signal becomes substantially equal to a second threshold value that is greater than the first threshold value; and an incidence time calculation circuit configured to calculate a starting time of the detected signal based on the first crossing time and the second crossing time which the starting time indicates when the waveform of the detected signal has started to rise and is used as the incidence time.

DESCRIPTION OF THE PREFERRED EMBODIMENTS

Preferred embodiments of the present invention are described below with reference to the accompanying drawings.

1. First Embodiment

Figure 2:
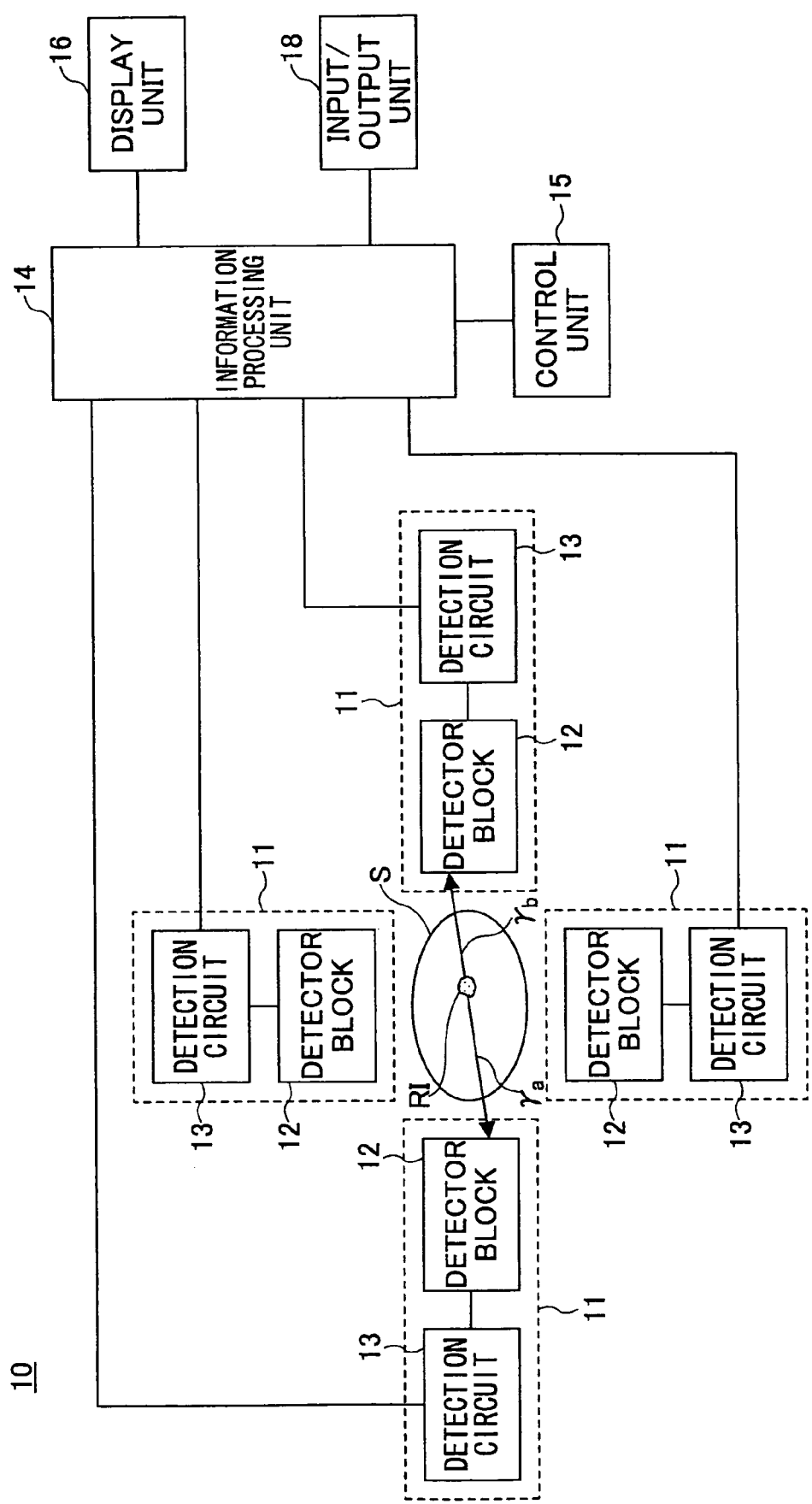
FIG. 2 is a block diagram illustrating an exemplary configuration of a PET apparatus according to a first embodiment of the present invention.

FIG. 2 is a block diagram illustrating an exemplary configuration of a PET apparatus according to a first embodiment of the present invention. As shown in FIG. 2, a PET apparatus 10 is configured so as to surround an object S and includes detection units 11 for detecting gamma rays each of which detection units 11 includes a detector block 12 and detection circuit 13; an information processing unit 14 for processing detection data and reconstructing image data showing detected positions of positron nuclides in the object S; a display unit 16 for displaying the image data; a control unit 15 for controlling the movement of the object S and the detection units 11; and an input/output unit 18 including a terminal for sending instructions to the information processing unit 14 and the control unit 15 and a printer for outputting image data.

Prior to examination, a diagnostic agent labeled by a positron nuclide RI is introduced into the object S. The detection units 11 detect gamma rays $\gamma_a$ and $\gamma_b$ emitted from the positron nuclide RI spatially and temporally. Each of the detection units 11 includes the detector block 12 including multiple detectors (described in detail later). The detector blocks 12 are positioned so as to surround the object S and detect the gamma rays $\gamma_a$ and $\gamma_b$ generated at the same time when the positron emitted from the positron nuclide RI is annihilated. The two gamma rays $\gamma_a$ and $\gamma_b$ are emitted at approximately 180 degrees to each other and therefore enter a pair of detectors of the detector blocks 12 facing to each other across the object S. Each of the pair of detectors receiving the gamma rays $\gamma_a$ and $\gamma_b$ generates an electrical signal (detected signal) corresponding to either the gamma ray $\gamma_a$ or $\gamma_b$, and sends the detected signal to the corresponding detection circuit 13.

The detection circuit 13, based on the detected signal, determines the time (incidence time) at which the gamma ray $\gamma_a$ or $\gamma_b$ has entered the detector and sends detection data including the incidence time and identification information (detector number, electrode number, etc.) of the detector to the information processing unit 14.

The information processing unit 14, based on the detection data, performs coincidence detection and reconstructs image data by an image reconstruction algorithm. In the coincidence detection, when the incidence times of two sets of detection data are substantially the same, the two sets of detection data are determined as valid and used as coincidence information. On the other hand, if the incidence times of two sets of detection data are different, the two sets of detection data are determined as invalid and discarded. The information processing unit 14 reconstructs image data by using an image reconstruction algorithm (for example, an expectation maximization algorithm) based on the detector numbers in the coincidence information and positional information of the corresponding detectors. The display unit 16 displays the reconstructed image data according to a request from the input/output unit 18.

As described above, the PET apparatus 10 detects gamma rays emitted from the positron nuclides RI accumulating preferentially in a part of the object S and reconstructs image data using valid detection data. The detection unit 11 of the PET apparatus 10 according to the first embodiment of the present invention includes the detection circuit 13 for determining the time at which a gamma ray enters a detector and has features as described below.

Figure 3:
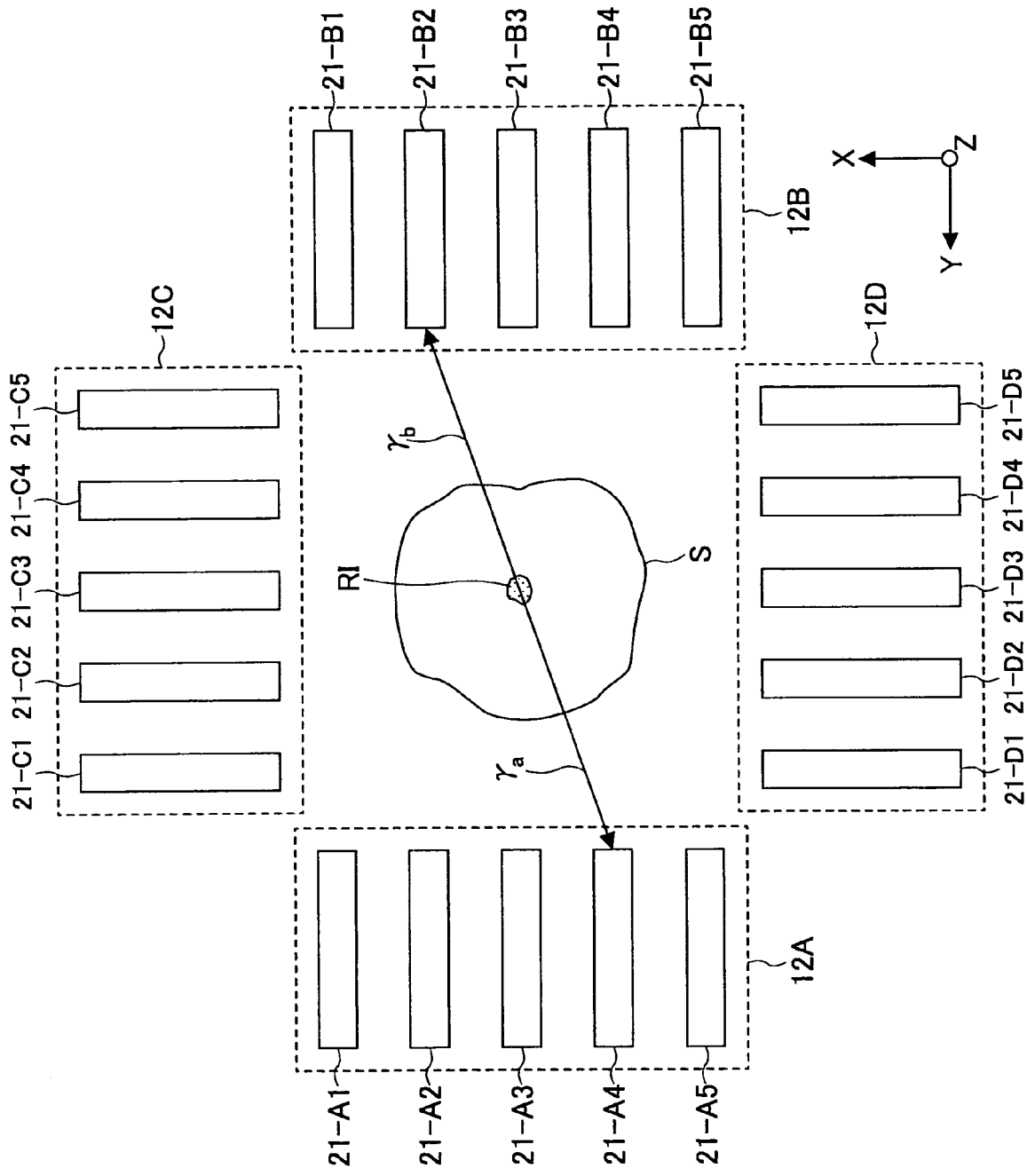
FIG. 3 is a drawing illustrating an exemplary configuration of detector blocks of a PET apparatus according to the first embodiment of the present invention.
Figure 4:
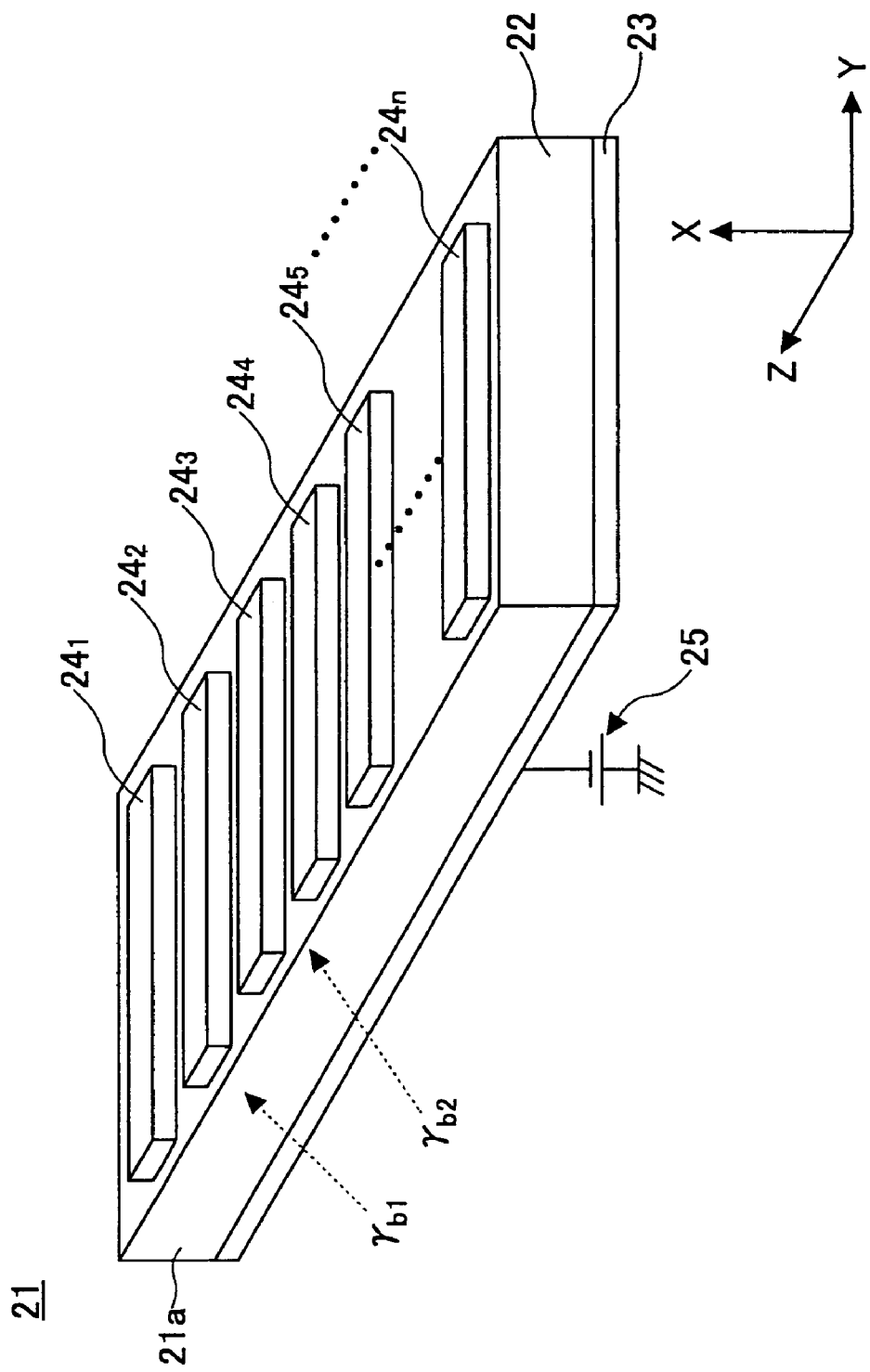
FIG. 4 is a perspective view of an exemplary detector.

FIG. 3 is a drawing illustrating an exemplary configuration of detector blocks of a PET apparatus according to the first embodiment of the present invention. FIG. 4 is a perspective view of an exemplary detector. The exemplary detector shown in FIG. 4 corresponds to a detector 21-B2 shown in FIG. 3.

As shown in FIG. 3, the detector blocks 12A through 12D are positioned so as to surround the object S. Each of the detector blocks 12A through 12D includes multiple detectors 21 (21-A, 21-B, 21-C, or 21-D) arranged at certain spacing. In the detector blocks 12A and 12B, the detectors 21-A1 through 21-A5 and the detectors 21-B1 through 21-B5 are arranged at certain spacing in the X axis direction. In the detector blocks 12C and 12D, the detectors 21-C1 through 21-C5 and the detectors 21-D1 through 21-D5 are arranged at certain spacing in the Y axis direction. Each of the detectors 21 has a certain width in the Z axis direction. The detector blocks 12A and 12B provide positional information of an incoming gamma ray in the X axis and Z axis directions. The detector blocks 12C and 12D provide positional information of an incoming gamma ray in the Y axis and Z axis directions. The arrangement of the detector blocks 12A through 12D is not limited to the arrangement described above as long as they are positioned so as to sandwich the object S. However, the detector blocks 12A through 12D are preferably arranged so as to form a circle surrounding the object S. Such a circular arrangement improves the efficiency of detecting gamma rays.

The number of the detectors 21 in each of the detector blocks 12 can be determined freely. For example, 32 of the detectors 21 can be provided in each of the detector blocks 12. In FIG. 3, the number of the detectors in each of the detector blocks 12 is set to five for descriptive purposes. The number of the detector blocks 12 and the number of the detectors 21 in each of the detector blocks 12 are preferably determined according to the size of an object to be examined and a spatial resolution to be achieved.

As shown in FIG. 4, the detector 21 includes a thin-plate like semiconductor crystal 22 and electrodes 23 and 24 formed on the upper and lower sides of the semiconductor crystal 22. The semiconductor crystal 22 may be made of, for example, cadmium telluride (CdTe), $Cd_{1-x}Zn_xTe$ (CZT), or thallium bromide (TlBr) that are sensitive to a 511 KeV gamma ray. CdTe may be doped with C1 to reduce leakage current. The semiconductor crystal 22 has, for example, a thickness of 0.5 mm, a width of 20 mm, and a depth of 10 mm.

The electrodes 23 and 24 may be made of Pt or In. The electrode 23 is shaped like a thin film and covers one side of the semiconductor crystal 22. The electrodes 24 are stripe-shaped and formed on the other side of the semiconductor crystal 22. A direct-current power supply 25 of about 80 V to 800 V is connected to the electrode 23 to apply a bias electric field to the semiconductor crystal 22. As shown in FIG. 4, the electrodes $24_1$ through $24_n$ are arranged at certain spacing in the Z axis direction. This arrangement makes it possible to determine an incidence position (in the Z axis direction) of a gamma ray entering the semiconductor crystal 22. In other words, the incidence position of a gamma ray in the Z axis direction can be obtained by determining the number (electrode number) of the electrode that carries an induced current induced by the gamma ray incidence. The width of each of the electrodes $24_1$ through $24_n$ may be 0.4 mm and the gap between two adjacent electrodes 24 may be 0.2 mm. The electrodes $24_1$ through $24_n$ are connected to the corresponding detection circuit 13 (illustrated in more detail in FIG. 5) by, for example, wires. The configuration of the detector 21 is not limited to that shown in FIG. 4. A detector may be a cuboid plate or hexahedron consisting of an array of detection elements aligned in the Z axis direction shown in FIG. 4 each of which detection elements is made up of electrodes and a rod-like semiconductor crystal which is long in the Y axis direction shown in FIG. 4.

The number of a detector (detector number) receiving a gamma ray and the number of an electrode (electrode number) where a detected signal appears are used as positional information indicating the incidence position of the gamma ray in the Z axis direction.

Exemplary operation of the detector 21 is described below with reference to FIG. 3 and FIG. 4. The gamma rays $\gamma_a$ and $\gamma_b$ are emitted from the positron nuclide RI in the object S at approximately 180 degrees to each other. Each of the gamma rays $\gamma_a$ and $\gamma_b$ enters the semiconductor crystal 22 of one of the detectors 21 (21-A4 or 21-B2 in FIG. 3) from an incidence plane 21a. Each of the gamma rays $\gamma_a$ and $\gamma_b$ entered the semiconductor crystal 22 forms electron-hole pairs matching its energy. When the semiconductor crystal 22 is made of CdTe, the energy required to create an electron-hole pair is approximately 5 eV. Therefore, when all the energy of a gamma ray is used to generate electron-hole pairs, approximately one million electron-hole pairs are generated. Since a negative voltage is applied to the electrode 23 of the semiconductor crystal 22 and a positive voltage is applied to the electrodes 24 of the semiconductor crystal 22, electrons generated in the semiconductor crystal 22 move to the electrodes 24 and holes move to the electrode 23. As a result, a detected signal appears on one of the electrodes. The holes and electrons move at the same time to the corresponding electrodes. However, in CdTe or CZT, the mobility of electrons is higher than that of holes. The detected signal appeared on any one of the electrodes $24_1$ through $24_n$ is sent to the detection circuit 13 (as shown in FIG. 5) connected to the electrodes $24_1$ through $24_n$.

The detected signal appears on one of the electrodes $24_1$ through $24_n$ that is closest to the incidence position of the gamma ray $\gamma_a$ or $\gamma_b$ entering the incident plane 21a. For example, when a gamma ray $\gamma_{b1}$ enters the incident plane 21a at a point close to the electrode $24_2$ as shown in FIG. 4, a detected signal appears on the electrode $24_2$. If the detected signal satisfies certain conditions in the detection circuit 13, the detector number and the number of the electrode $24_2$ (electrode number) are used as positional information indicating the incidence position of the gamma ray $\gamma_{b1}$.

As another example, when a gamma ray $\gamma_{b2}$ enters the incident plane 21a at a point approximately the same distance from the electrodes $24_3$ and $24_4$ as shown in FIG. 4, detected signals appear on both of the electrodes $24_3$ and $24_4$. If the detected signals satisfy certain conditions in the detection circuit 13, the detector number and the numbers of the electrodes $24_3$ and $24_4$ (electrode numbers) are used as positional information indicating the incidence position of the gamma ray $\gamma_{b2}$. In this example, since electron charges are divided between the electrodes $24_3$ and $24_4$, the maximum pulse height of each of the detected signals becomes lower than that of the detected signal corresponding to the gamma ray $\gamma_{b1}$ in the previous example. Also, the rise angle of each of the detected signals (increase rate of pulse height per unit time) becomes smaller. The detection circuit 13 described below can accurately calculate the starting time of such a detected signal.

Figure 5:
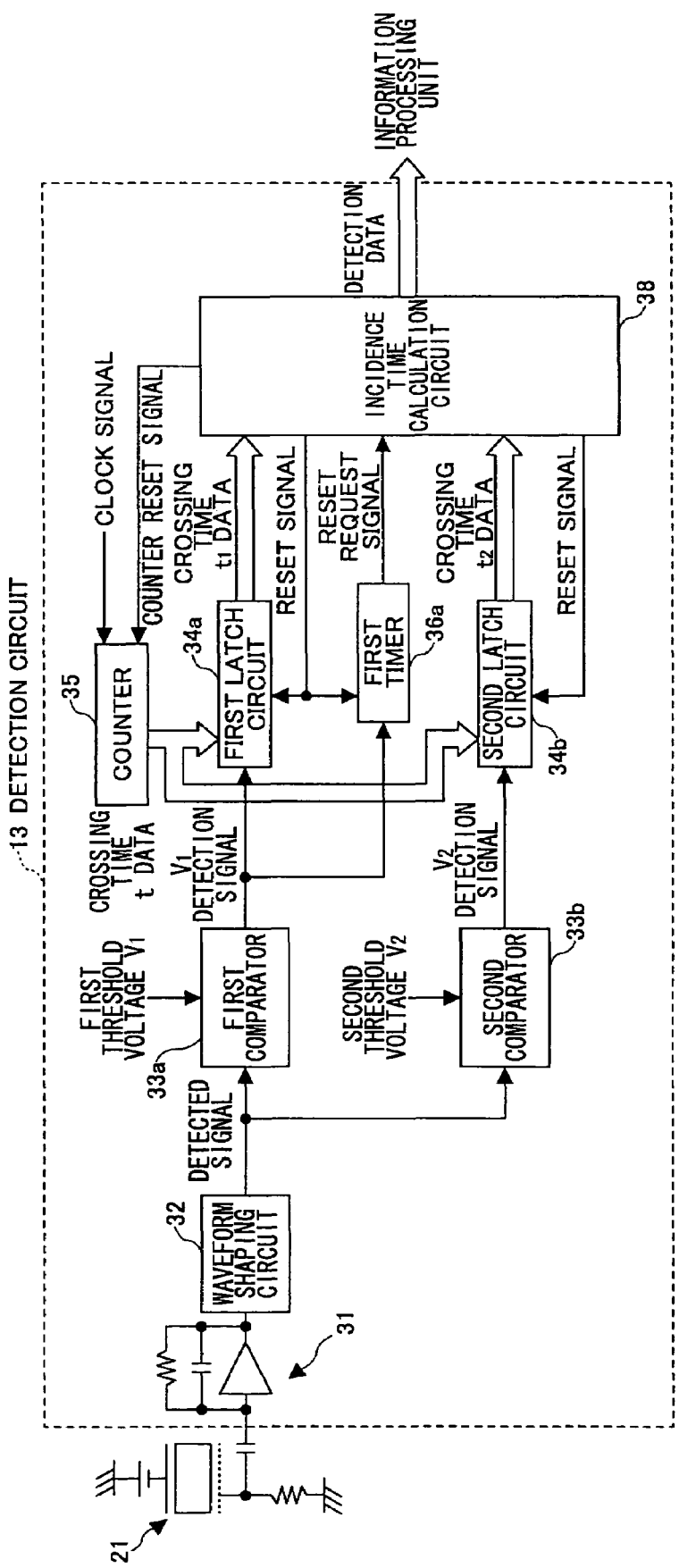
FIG. 5 is a block diagram illustrating an exemplary detection circuit of a PET apparatus according to the first embodiment of the present invention.

FIG. 5 is a block diagram illustrating an exemplary detection circuit of a PET apparatus according to the first embodiment of the present invention. The detector 21 is also shown in FIG. 5.

As shown in FIG. 5, the detection circuit 13 includes a preamplifier circuit 31, a waveform shaping circuit 32, a first comparator 33a and a first latch circuit 34a for determining a crossing time $t_1$ at which a detected signal reaches a first threshold voltage $V_1$, a second comparator 33b and a second latch circuit 34b for determining a crossing time $t_2$ at which the detected signal reaches a second threshold voltage $V_2$, an incidence time calculation circuit 38 for calculating the starting time of the detected signal from the crossing time $t_1$ (crossing time $t_1$ data) and the crossing time $t_2$ (crossing time $t_2$ data), a counter 35 for supplying crossing time data, and a first timer 36a.

The preamplifier circuit 31 receives charges (a detected signal) from one of the electrodes 24 (for example, one of the electrodes $24_1$ through $24_n$ shown in FIG. 4) of the detector 21. Then the preamplifier circuit 31 converts the received charges into a voltage, amplifies the voltage, and sends the voltage as a detected signal.

The waveform shaping circuit 32 shapes the waveform of the detected signal received from the preamplifier circuit 31 into a waveform suitable for processing. For the waveform shaping circuit 32, a passive filter consisting of a resistor and a capacitor or an active filter consisting of an operational amplifier, a resistor, and a capacitor may be used. The configuration of the waveform shaping circuit 32 is not limited to a specific embodiment. The waveform shaping circuit 32 may be made up of a high-pass filter, a low-pass filter, or a combination of a high-pass filter and a low-pass filter. When a combination of a high-pass filter and a low-pass filter is used to form the waveform shaping circuit 32, the order of the low-pass filter is preferably in the range of first to third that provides good linearity of a rising waveform. For example, the waveform shaping circuit 32 may be composed of a first-order high-pass filter and a first-order low-pass filter, or a first-order high-pass filter and a third-order high-pass filter.

The first comparator 33a compares the detected signal received from the waveform shaping circuit 32 and the first threshold voltage $V_1$ and, when the detected signal reaches the first threshold voltage $V_1$, sends a $V_1$ detection signal to the first latch circuit 34a.

The first latch circuit 34a also receives crossing time t data indicating a crossing time t constantly from the counter 35. The first latch circuit 34a saves the crossing time t data corresponding to the time at which the $V_1$ detection signal is received and sends the saved crossing time t data as crossing time $t_1$ data to the incidence time calculation circuit 38.

In the second comparator 33b, the second threshold voltage $V_2$ is set as the threshold voltage. The second threshold voltage $V_2$ is higher than the first threshold voltage $V_1$. The second comparator 33b compares the detected signal received from the waveform shaping circuit 32 and the second threshold voltage $V_2$ and, when the detected signal reaches the second threshold voltage $V_2$, sends a $V_2$ detection signal to the second latch circuit 34b. In other words, the second comparator 33b determines the crossing time at which the pulse height of the rising waveform of a detected signal reaches the second threshold voltage $V_2$ that is higher than the first threshold voltage $V_1$.

The second latch circuit 34b also receives crossing time t data indicating a crossing time t constantly from the counter 35. The second latch circuit 34b saves the crossing time t data corresponding to the time at which the $V_2$ detection signal is received and sends the saved crossing time t data as crossing time $t_2$ data to the incidence time calculation circuit 38.

The incidence time calculation circuit 38 calculates a starting time to of the detected signal based on the crossing time $t_0$ data, the crossing time $t_2$ data, the first threshold voltage $V_1$, and the second threshold voltage $V_2$. The method of calculating the starting time $t_0$ is described later. The incidence time calculation circuit 38 sends detection data including the starting time $t_0$, the detector number, and the electrode number to the information processing unit 14.

The first timer 36a starts measuring time when the $V_1$ detection signal is received from the first comparator 33a. When a specified amount of time $\tau 1$ passes, the first timer 36a sends a reset request signal to the incidence time calculation circuit 38. In other words, if the pulse height of the detected signal does not reach the second threshold voltage $V_2$ within a certain period of time, the first timer 36a sends a reset request signal to make circuits ready to detect a next gamma ray. The length of the time $\tau 1$ is determined according to the time a detected signal takes to reach its peak from the starting time of the rising waveform.

When receiving the reset request signal before receiving the crossing time $t_2$ data, the incidence time calculation circuit 38 discards the crossing time $t_1$ data already received. Then, the incidence time calculation circuit 38 sends reset signals to the first latch circuit 34a and the first timer 36a to make them ready to receive a next detected signal.

The counter 35 receives a clock signal having a certain frequency from a clock circuit (not shown) and sends the crossing time t data to the first latch circuit 34a and the second latch circuit 34b according to the clock signal. The number of bits of the crossing time t data is not especially limited. For example, the crossing time t data have 48 bits and the least significant bit corresponds to 10 nanoseconds. With 48 bits, the counter 35 is able to provide crossing time data for 780 hours after the start of measurement.

The detection circuit 13 may be formed as a discrete circuit. However, it is preferable to form the detection circuit 13 on a semiconductor chip to reduce its size. When the detection circuit 13 is formed on a semiconductor chip, the first threshold voltage $V_1$ and the second threshold voltage $V_2$ may be either preset in the semiconductor chip or supplied from the outside of the semiconductor chip.

Figure 6:
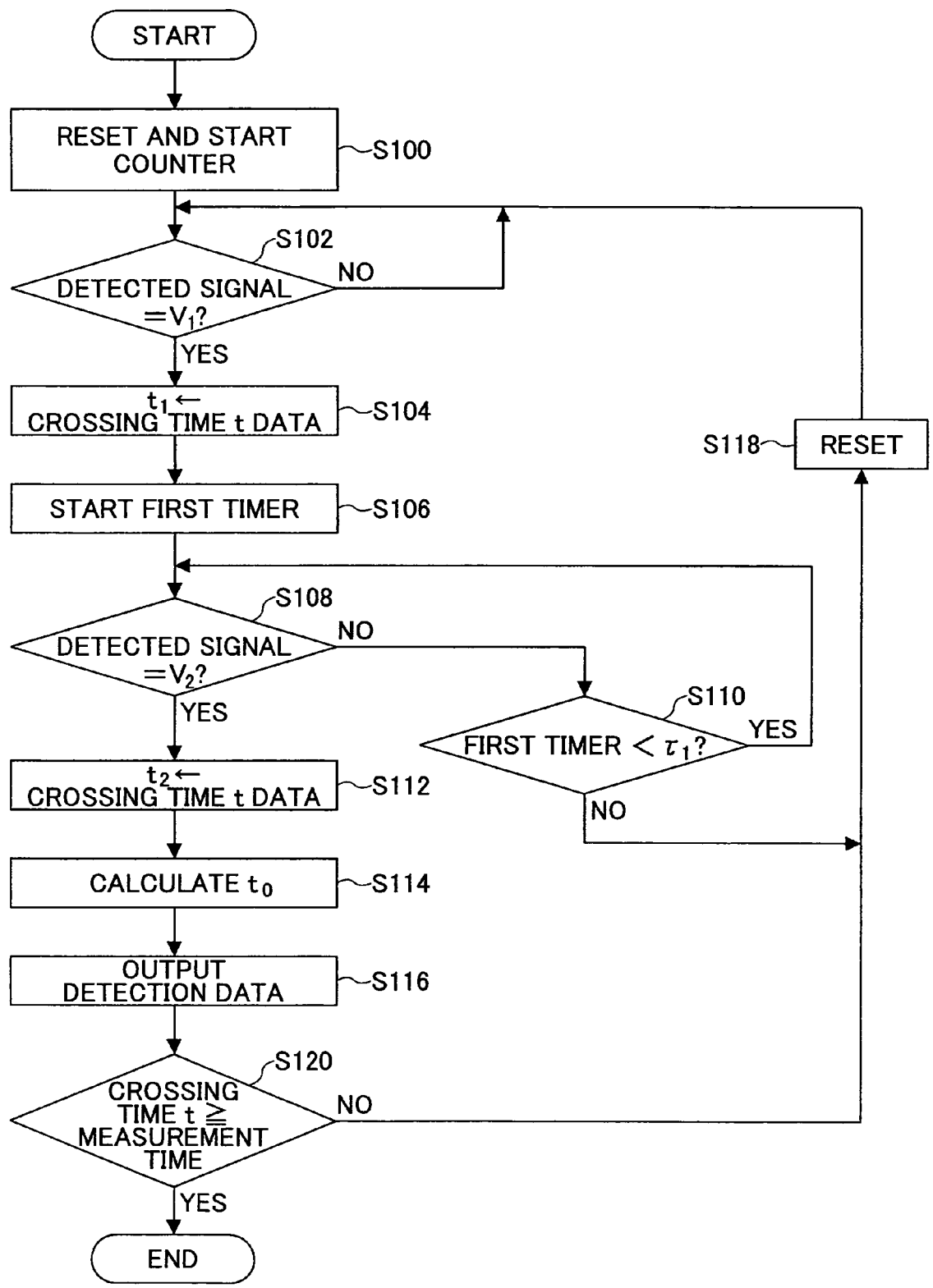
FIG. 6 is a flowchart illustrating exemplary operation of a detection circuit of a PET apparatus according to the first embodiment of the present invention.
Figure 7:
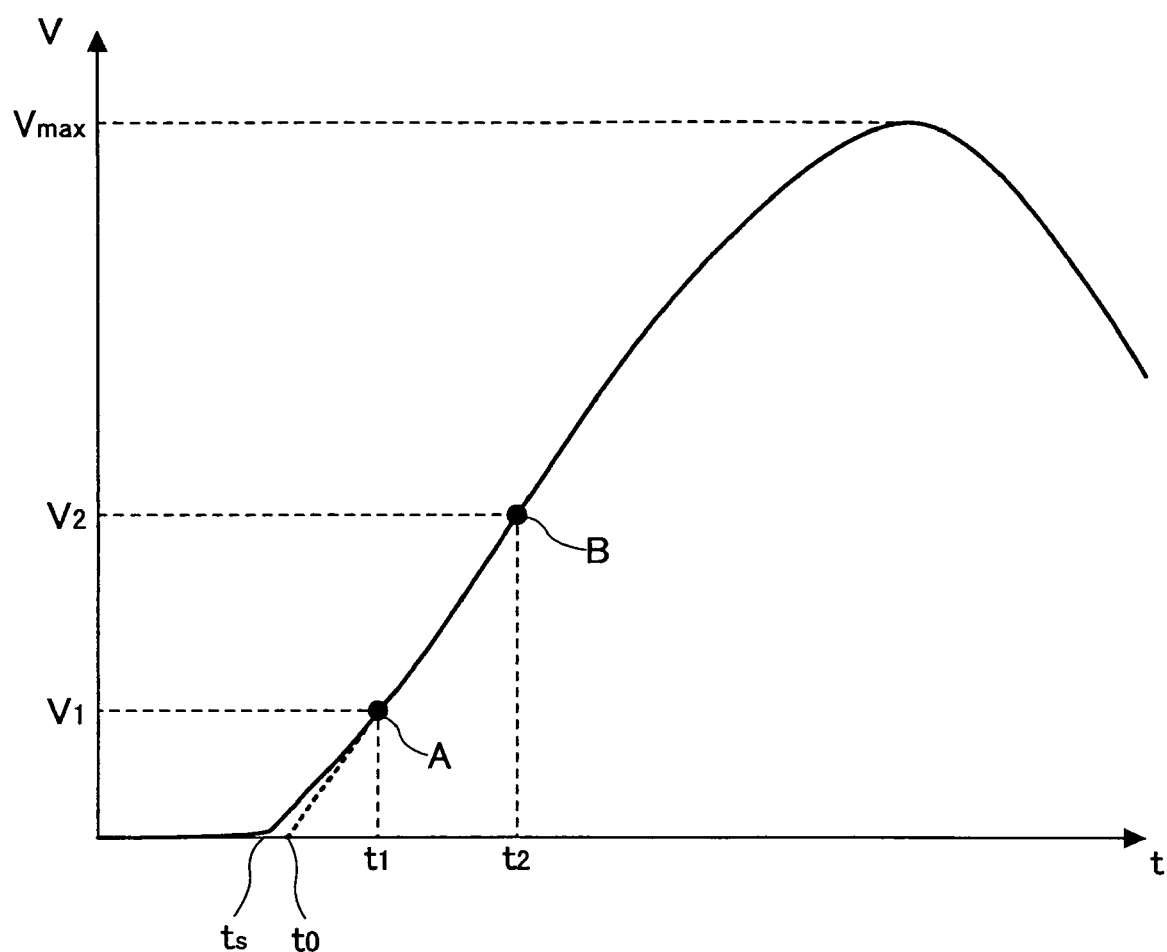
FIG. 7 is a graph used to describe an exemplary method of calculating a starting time of a detected signal.

FIG. 6 is a flowchart illustrating exemplary operation of a detection circuit of a PET apparatus according to the first embodiment of the present invention. FIG. 7 is a graph used to describe an exemplary method of calculating a starting time of a detected signal. In FIG. 7, the waveform of a detected signal is indicated by a solid line.

The descriptions below are made with reference to FIGS. 5, 6, and 7. Before starting examination, the counter 35 is reset and caused to start sending crossing time t data (S100).

The first comparator 33a waits until the pulse height of a detected signal reaches the first threshold voltage $V_1$ (S102). When the waveform of the detected signal starts to rise at a crossing time $t_s$ (actual starting time) as shown in FIG. 7 and then its pulse height reaches the first threshold voltage $V_1$ (point A show in FIG. 7), the first comparator 33a sends a $V_1$ detection signal to the first latch circuit 34a and the first timer 36a.

The first latch circuit 34a saves crossing time t data corresponding to the time at which the V1 detection signal is received as crossing time $t_1$ data (S104). Then, the first latch circuit 34a sends the saved crossing time $t_1$ data to the incidence time calculation circuit 38. The first timer 36a starts measuring time when the $V_1$ detection signal is received.

If the amount of time measured by the first timer 36a exceeds time $\tau 1$ (S110) before the pulse height of the detected signal reaches the second threshold voltage $V_2$ (S108), the first timer 36a sends a reset request signal to the incidence time calculation circuit 38. When receiving the reset request signal, the incidence time calculation circuit 38 sends reset signals to the first latch circuit 34a and the first timer 36a to make them ready to receive a next detected signal and discards the crossing time $t_1$ data (S118).

On the other hand, if the pulse height of the detected signal reaches the second threshold voltage $V_2$ (point B shown in FIG. 7) before the amount of time measured by the first timer 36a exceeds time $\tau 1$, the second comparator 33b sends $V_2$ detection signal to the second latch circuit 34b. The second latch circuit 34b saves crossing time t data corresponding to the time at which the $V_2$ detection signal is received as crossing time $t_2$ data (S112). Then, the second latch circuit 34b sends the saved crossing time $t_2$ data to the incidence time calculation circuit 38.

The incidence time calculation circuit 38 calculates a starting time $t_0$ of the detected signal based on the crossing time $t_1$ data, the crossing time $t_2$ data, the first threshold voltage $V_1$, and the second threshold voltage $V_2$ (S114).

The starting time $t_0$ can be calculated, for example, by linear regression as described below.

The relationship between a pulse height V of a detected signal that has begun to rise and a crossing time t is expressed by the following equation:

$$t=\alpha V+t_0 \quad (1)$$

In equation (1), a is a proportionality coefficient. The starting time $t_0$ can be obtained by inserting the crossing time $t_1$ data ($t_1$), the crossing time $t_2$ data ($t_2$), the first threshold voltage $V_1$, and the second threshold voltage $V_2$ in equation (1) as follows:

$$t_0=(V_2 t_1 - V_1 t_2)/(V_2-V_1) \quad (2)$$

As shown in FIG. 7, the pulse height of the detected signal that has begun to rise can be approximated by a linear function of the crossing time t. Therefore, by using linear regression, a starting time $t_0$ having a small deviation from the actual starting time $t_s$ can be obtained. When a high-pass filter and a first (second or third)-order low-pass filter is used for the waveform shaping circuit 32 shown in FIG. 5, the rising waveform of the detected signal can be expressed by a linear function of time. Therefore, by using the waveform shaping circuit 32 as described above, a starting time $t_0$ having a minimum deviation from the actual starting time $t_s$ can be obtained.

Also, using linear regression to calculate starting times $t_0$ of detected signals having different peak values makes it possible to reduce fluctuations of deviations from actual starting times $t_s$.

The first threshold voltage $V_1$ and the second threshold voltage $V_2$ are preferably selected from within a range where the rising waveform of a detected signal can be approximated by a linear function of the crossing time t. The first threshold voltage $V_1$ and the second threshold voltage $V_2$ may also be determined by selecting appropriate voltages based on the noise levels.

The first threshold voltage $V_1$ is preferably determined so that the ratio $V_1/V$max of the first threshold voltage $V_1$ to the maximum pulse height Vmax of a detected signal falls within a range between 1/64 and 1/5 (corresponding to a gamma ray energy level of between 8 keV and 100 keV). When the ratio $V_1/V$max is lower than 1/64, probability of malfunctions caused by background noises may increase. The maximum pulse height Vmax is the maximum pulse height of a detected signal when all the energy (511 keV) of an incoming gamma ray is used to generate electron-hole pairs.

The second threshold voltage $V_2$ is preferably set to a value two times higher than the first threshold voltage $V_1$ so that the ratio $V_2/V$max falls within a range between 1/32 and 1/2.5 (corresponding to a gamma ray energy level of between 16 keV and 200 keV).

The incidence time calculation circuit 38 uses the calculated starting time $t_0$ as the incidence time $t_0$ indicating when the gamma ray has entered the detector 21 and sends detection data including the incidence time $t_0$, the detector number, and the electrode number to the information processing unit 14 (S116). The detector number and the electrode number may be preset in the incidence time calculation circuit 38. The information processing unit 14, based on sets of detection data sent from multiple detection circuits 13, performs coincidence detection and reconstructs image data using an image reconstruction algorithm.

Then, the incidence time calculation circuit 38 sends reset signals to the first latch circuit 34a, the first timer 36a, and the second latch circuit 34b to reset these circuits (S118), thereby making the detection circuit 13 ready to receive a next detected signal. When the crossing time t exceeds specified measurement time, examination is terminated (S120).

According to the first embodiment of the present invention, the detection circuit 13 determines two time points at which the pulse height of the rising waveform of a detected signal reaches the first threshold voltage $V_1$ and the second threshold voltage $V_2$ and calculates the starting time $t_0$ or the incidence time of the detected signal. Such a mechanism makes it possible to implement the detection circuit 13 without using the delay circuit 101 of the conventional detection circuit 100 as shown in FIG. 1 and to implement the detection circuit 13 with a simple configuration including the first comparator 33a, the first latch circuit 34a, the second comparator 33b, and the second latch circuit 34b that detect the pulse height of a detected signal.

Figure 1:
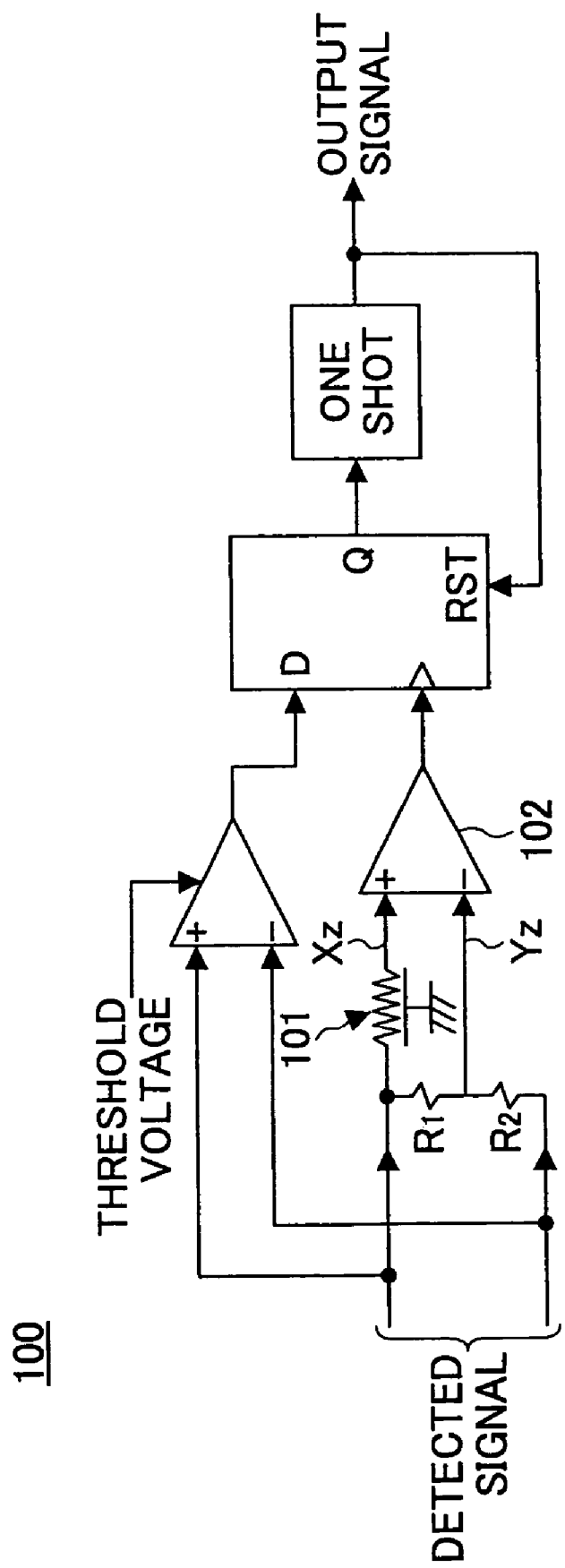
FIG. 1 is a circuit diagram illustrating a part of a conventional detection circuit.

Also, according to the first embodiment of the present invention, when the detection circuit 13 is formed on a semiconductor chip, the detection circuit 13 can be implemented without using the delay circuit 101 of the conventional detection circuit 100 as shown in FIG. 1. As described above, the first embodiment eliminates the need to rebuild a detection circuit to change the delay time of a delay circuit, thereby reducing the production costs and production time of a PET apparatus.

The detection circuit 13 may include an additional comparator and an additional latch circuit that measure the crossing time at which the pulse height of the rising waveform of a detected signal reaches a voltage higher than the second threshold voltage $V_2$ so as to calculate a starting time by linear regression based on three crossing times. In this case, a regression method of a higher order may be used.

Also, although not shown in the figures, the detection circuit 13 may include an X-ray source that is rotatable around the object S shown in FIG. 2. The X-ray source is preferably capable of emitting an X-ray having an energy level lower than 511 keV, for example, about 50 keV. The X-ray is detected by the detector 21. The first comparator 33a and the first latch circuit 34a shown in FIG. 5. obtain crossing time $t_1$ data indicating the incidence time of the X-ray. The incidence time calculation circuit 38 generates detection data based on the obtained crossing time $t_1$ data. The detection data are processed by the information processing unit 14 to obtain the formation of the object S. For example, a PET apparatus having such an X-ray source makes it possible to determine the positional relationship between a body part where positron nuclides are accumulated and surrounding body parts.

2. Second Embodiment

A PET apparatus according to a second embodiment of the present invention is described below. A PET apparatus according to the second embodiment of the present invention has a configuration similar to that of a PET apparatus according to the first embodiment except the configuration of the detection circuit.

The detector blocks and detectors of a PET apparatus according to the second embodiment have configurations similar to those of the detector blocks and detectors of a PET apparatus according to the first embodiment. Therefore, descriptions of parts having similar configurations are omitted.

Figure 8:
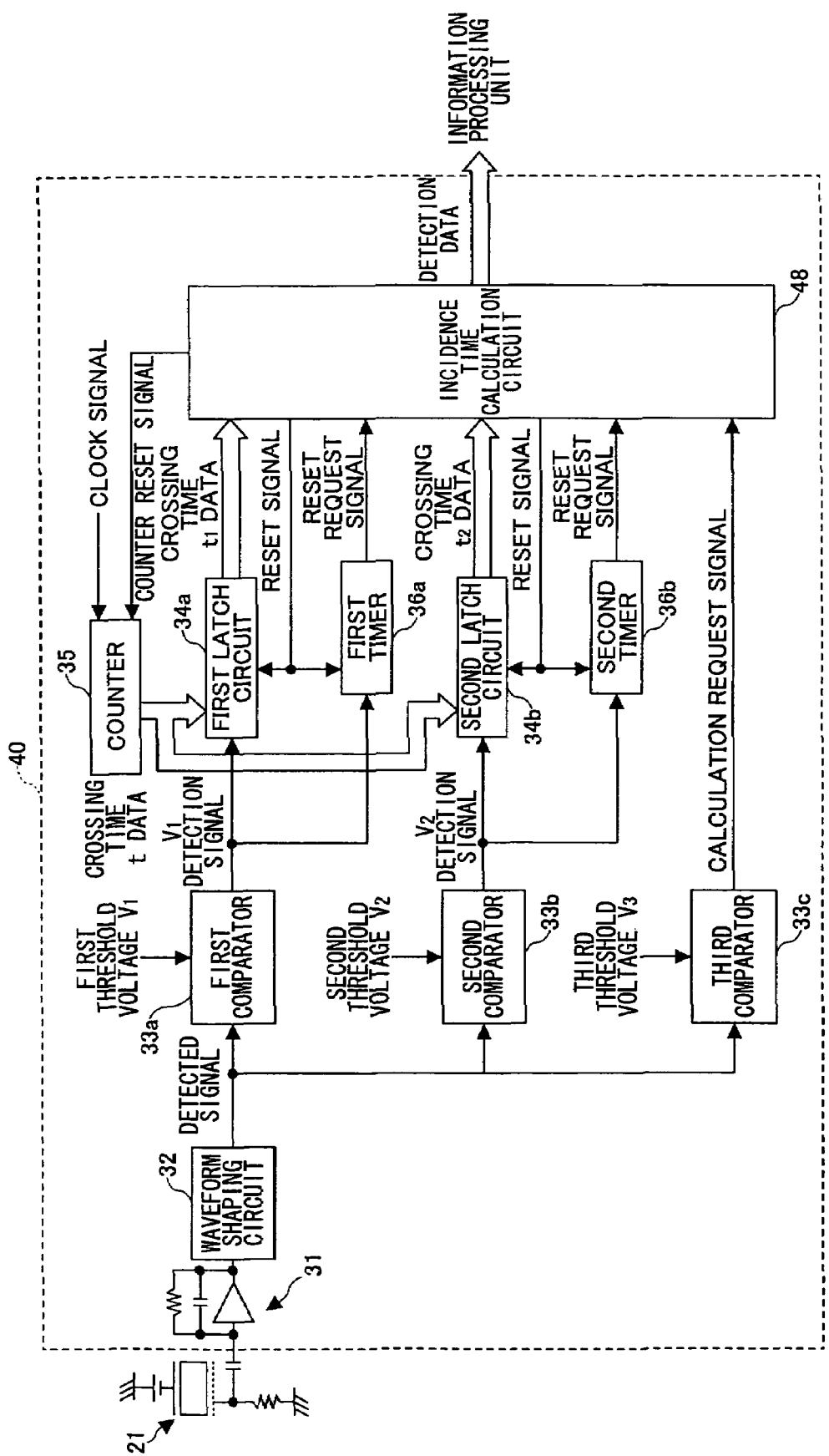
FIG. 8 is a block diagram illustrating an exemplary detection circuit of a PET apparatus according to a second embodiment of the present invention.

FIG. 8 is a block diagram illustrating an exemplary detection circuit of a PET apparatus according to the second embodiment of the present invention. In FIG. 8, the same reference numbers are used for parts corresponding to those shown in FIG. 5, and descriptions of those parts are omitted.

As shown in FIG. 8, the detection circuit 40 includes a preamplifier circuit 31, a waveform shaping circuit 32, a first comparator 33a and a first latch circuit 34a for determining a crossing time $t_1$ at which a detected signal reaches a first threshold voltage $V_1$, a second comparator 33b and a second latch circuit 34b for determining a crossing time $t_2$ at which the detected signal reaches a second threshold voltage $V_2$, a third comparator 33c for comparing the detected signal with a third threshold voltage $V_3$, an incidence time calculation circuit 48 for calculating the starting time $t_0$ of the detected signal from the crossing time $t_1$ (crossing time $t_1$ data) and the crossing time $t_2$ (crossing time $t_2$ data), a counter 35 for supplying crossing time data, a first timer 36a, and a second timer 36b. In the detection circuit 40 according to the second embodiment, the third comparator 33c and the second timer 36b are provided as additional components. The incidence time calculation circuit 48 has an additional function in addition to the functions provided by the incidence time calculation circuit 38 shown in FIG. 5.

In the third comparator 33c, the third threshold voltage $V_3$ is set as the threshold voltage. The third threshold voltage $V_3$ is higher than the second threshold voltage $V_2$. For example, the third threshold voltage $V_3$ is set at a voltage corresponding to a gamma ray energy level of between 200 keV and 300 keV. The third comparator 33c compares the detected signal received from the waveform shaping circuit 32 with the third threshold voltage $V_3$ and, when the detected signal becomes substantially equal to or higher than the third threshold voltage $V_3$, sends a calculation request signal requesting the calculation of a starting time $t_0$ or an incidence time $t_0$ the incidence time calculation circuit 48.

The second timer 36b starts measuring time when a $V_2$ detection signal is received from the second comparator 33b. When a specified amount of time $\tau 2$ passes, the second timer 36b sends a reset request signal to the incidence time calculation circuit 48. In other words, if the pulse height of the detected signal does not reach the third threshold voltage $V_3$ within a certain period of time, the second timer 36b sends a reset request signal to make circuits ready to detect a next gamma ray. The length of the time $\tau 2$ is determined according to the time a detected signal takes to reach its peak from the starting time of the rising waveform.

When receiving the calculation request signal from the third comparator circuit 33c, the incidence time calculation circuit 48 calculates a starting time $t_0$. The incidence time calculation circuit 38 according to the first embodiment shown in FIG. 5 calculates a starting time $t_0$ in response to crossing time $t_2$ data. On the other hand, the incidence time calculation circuit 48 calculates a starting time $t_0$ in response to the calculation request signal.

The incidence time calculation circuit 48 handles crossing time $t_1$ data in a similar manner to the incidence time calculation circuit 38. When receiving the reset request signal from the second timer 36b, the incidence time calculation circuit 48 discards the crossing time $t_1$ data and the crossing time $t_2$ data and waits for a next detected signal.

As described above, when a detected signal does not reach the third threshold voltage $V_3$, the detection circuit 40 does not obtain detection data from the detected signal. This makes it possible to detect only gamma rays having an energy level higher than a specified level, thereby improving the reliability of examination using a PET apparatus.

Figure 9:
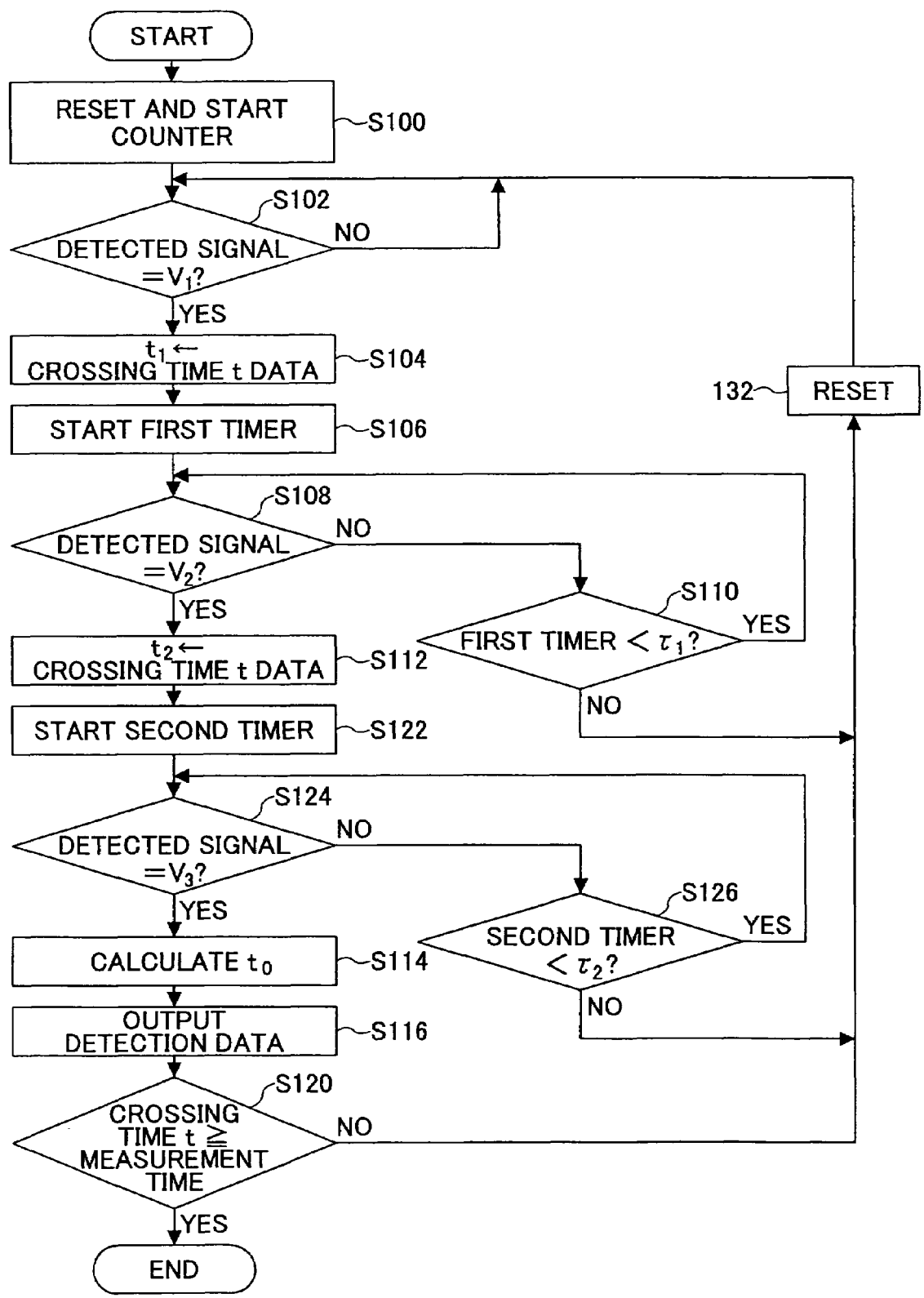
FIG. 9 is a flowchart illustrating exemplary operation of a detection circuit of a PET apparatus according to the second embodiment of the present invention.
Figure 10A:
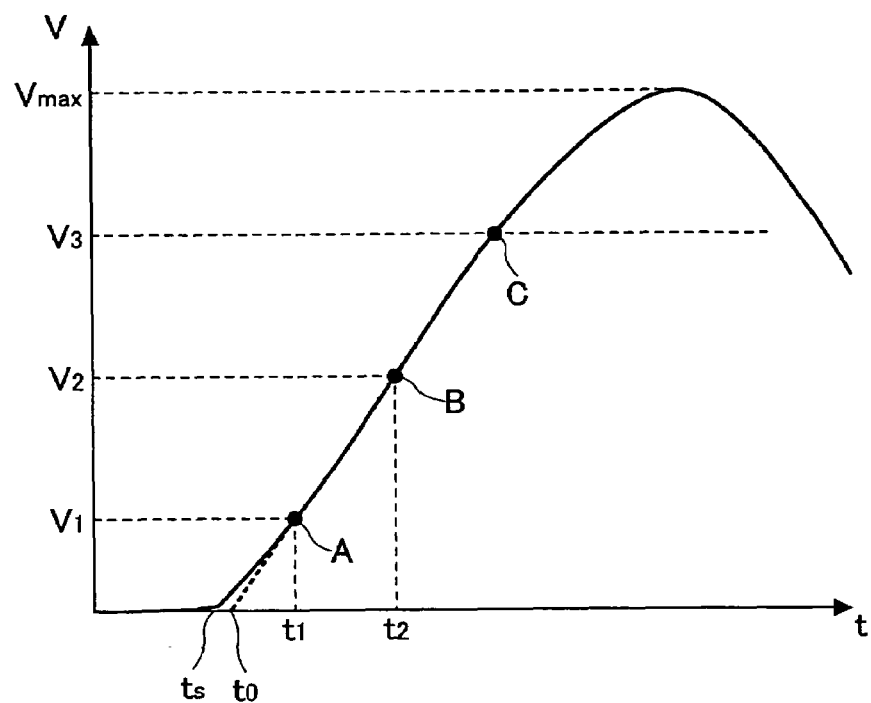
FIGS. 10A and 10B are graphs used to describe another exemplary method of calculating a starting time of a detected signal.
Figure 10B:
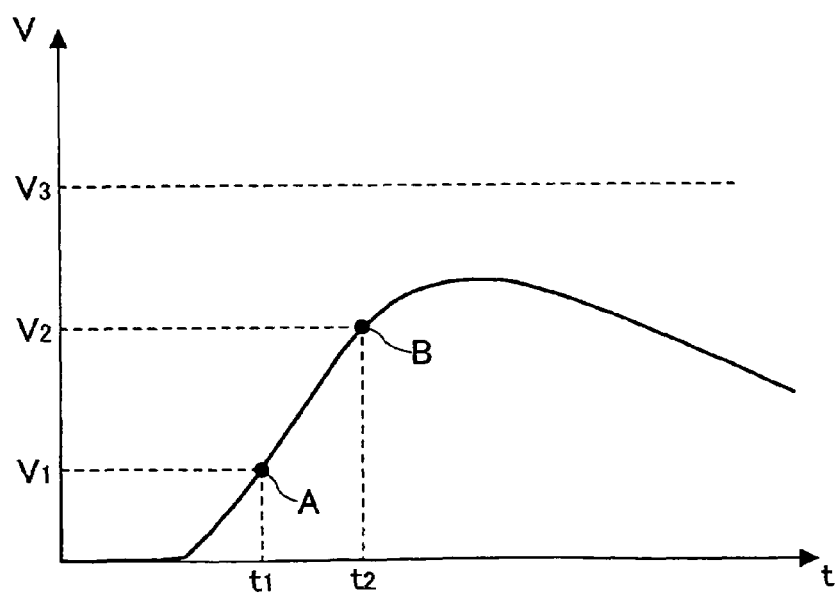

FIG. 9 is a flowchart illustrating exemplary operation of a detection circuit of a PET apparatus according to the second embodiment of the present invention. FIGS. 10A and 10B are graphs used to describe another exemplary method of calculating the starting time of a detected signal. In FIGS. 10A and 10B, the waveforms of detected signals are indicated by solid lines.

The descriptions below are made with reference to FIGS. 8, 9, 10A, and 10B. In FIG. 9, steps (S100 through S112) from the start of the process till the transmission of crossing time $t_2$ data are substantially the same as the steps shown in FIG. 6 illustrating the exemplary operation of the detection circuit 13 according to the first embodiment. Therefore, descriptions of those steps are omitted.

The second timer 36b starts measuring time when the $V_2$ detection signal is received (S122). If the amount of time measured by the second timer 36b exceeds the time $\tau 2$ (S126) before the pulse height of the detected signal reaches the third threshold voltage $V_3$ (S124), the second timer 36b sends a reset request signal to the incidence time calculation circuit 48. Then, the incidence time calculation circuit 48 sends reset signals to the first latch circuit 34a, the first timer 36a, the second latch circuit 34b, and the second timer 36b to make them ready to receive a next detected signal, and discards the crossing time $t_1$ data and the crossing time $t_2$ data (S132).

On the other hand, if the pulse height of the detected signal reaches the third threshold voltage $V_3$ (point C shown in FIG. 10A) (S124) before the amount of time measured by the second timer 36b exceeds the time $\tau 2$, the third comparator 33c sends a calculation request signal to the incidence time calculation circuit 48.

In other words, the third comparator 33c generates a calculation request signal when the detected signal becomes substantially equal to or higher than the third threshold voltage $V_3$ as shown in FIG. 10A. Also, when the peak value of the detected signal is lower than the third threshold voltage $V_3$, the second timer 36b sends a reset request signal to the incidence time calculation circuit 48. Therefore, the starting time to is not calculated and the detection circuit 40 waits for a next detected signal. With the above mechanism, the detection circuit 40 cancels the process of obtaining detection data of an invalid detected signal at an early stage, thereby improving the efficiency of obtaining valid detection data.

When receiving the calculation request signal, the incidence time calculation circuit 48 calculates the starting time $t_0$ of the detected signal based on the crossing time $t_1$ data, the crossing time $t_2$ data, the first threshold voltage $V_1$, and the second threshold voltage $V_2$ (S114). The method of calculating the starting time $t_0$ is substantially the same as in the first embodiment and therefore description of the calculation method is omitted here.

The incidence time calculation circuit 48 uses the calculated starting time $t_0$ as the incidence time to indicating when the gamma ray has entered the detector 21 and sends detection data including the incidence time to, the detector number, and the electrode number to the information processing unit 14 (S116). The detector number and the electrode number may be preset in the incidence time calculation circuit 48. The information processing unit 14, based on sets of detection data sent from multiple detection circuits 40, performs coincidence detection and reconstructs image data using an image reconstruction algorithm.

Then, the incidence time calculation circuit 48 sends reset signals to the first latch circuit 34a, the first timer 36a, the second latch circuit 34b, and the second timer 36b to reset these circuits (S132). This reset operation makes the detection circuit 40 ready to receive a next detected signal. When the crossing time t exceeds specified measurement time, examination is terminated (S120).

A PET apparatus according to the second embodiment provides substantially the same functions as a PET apparatus according to the first embodiment of the present invention. In a PET apparatus according to the second embodiment, a detected signal that does not reach the third threshold voltage $V_3$ is discarded as invalid. This mechanism improves the reliability of examination. Also, in a PET apparatus according to the second embodiment, a detected signal that does not reach the third threshold voltage $V_3$ is discarded at an early stage of the detection process so as to be able to receive a next detected signal. This mechanism improves the efficiency of detecting gamma rays.

3. Third Embodiment

A third embodiment of the present invention is described below. In the third embodiment, some changes are made to the detection circuit 40 according to the second embodiment.

Figure 11:
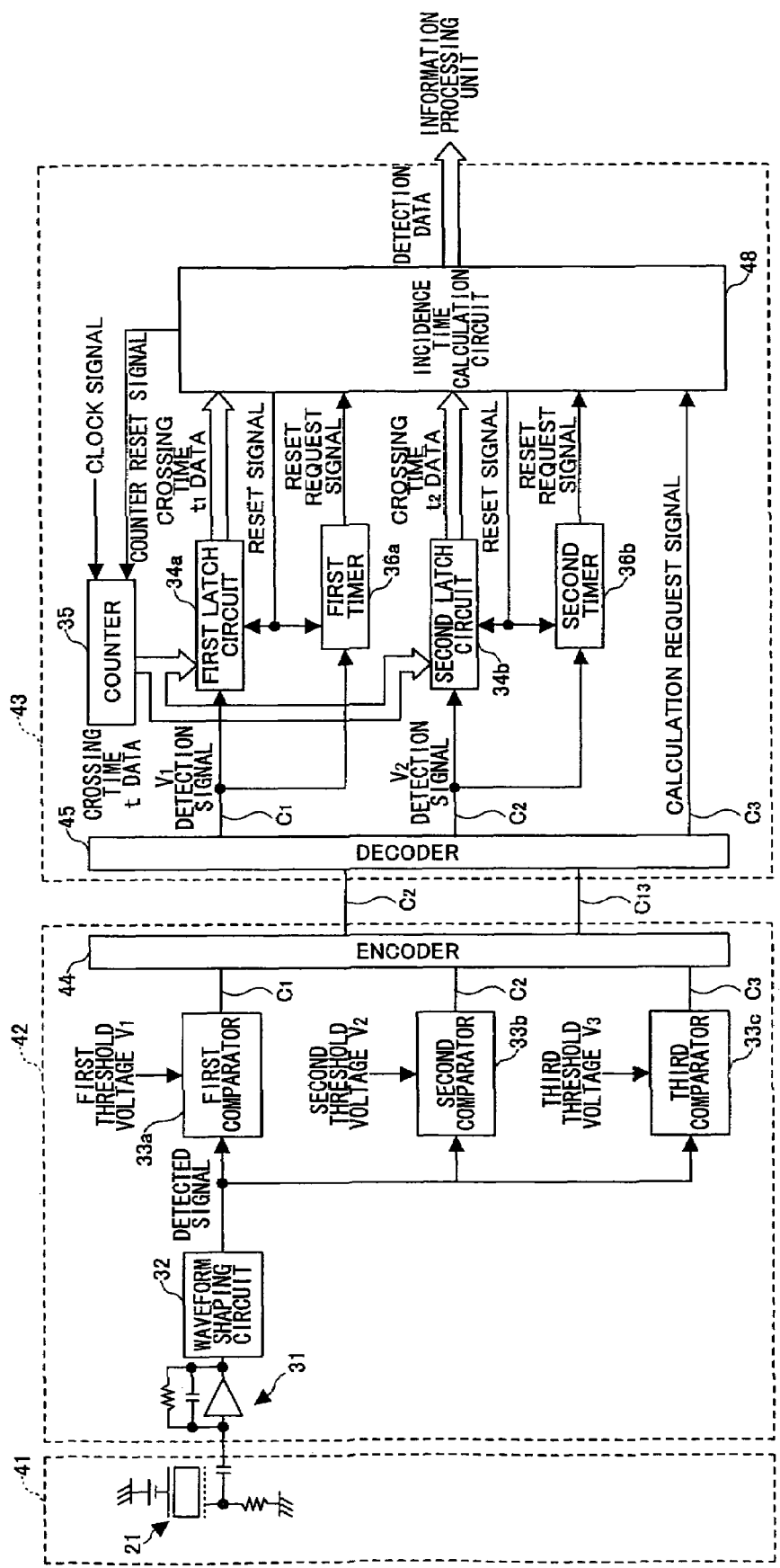
FIG. 11 is a block diagram illustrating an exemplary detection circuit of a PET apparatus according to a third embodiment of the present invention.

FIG. 11 is a block diagram illustrating an exemplary detection circuit of a PET apparatus according to a third embodiment of the present invention. In FIG. 11, the same reference numbers are used for parts corresponding to those shown in FIG. 8.

An exemplary detection circuit of a PET apparatus shown in FIG. 11 is formed on three substrates 41, 42, 43. On the substrate 41, a crystalline application specific integrated circuit (ASIC) is formed. On the substrate 42, a preamplifier circuit 31, a waveform shaping circuit 32, a first comparator 33a, a second comparator 33b, a third comparator 33c, and an encoder 44 are formed. On the substrate 43, a first latch circuit 34a, a second latch circuit 34b, a counter 35, a first timer 36a, a second timer 36b, a decoder 45, and an incidence time calculation circuit 48 are formed.

The detector 21 of the detector block 12 is essentially the same as that shown in FIG. 4. Detected signals are output from the electrodes of the detector 21. In FIG. 11, only one detection circuit is shown for descriptive purposes. However, in an actual PET apparatus, multiple detection circuits are formed on the substrates 42 and 43 to process detected signals sent from multiple detectors 21 of the detector block 12.

For example, if the detector block 12 includes 32 of the detectors 21, the same number of detection circuits are formed on the substrates 42 and 43.

In the exemplary detection circuit according to the third embodiment, signals from the first comparator 33a, the second comparator 33b, and the third comparator 33c are output to the encoder 44, the decoder 45 decodes the signals from the encoder 44, the decoded signals from the decoder 45 are output to the first latch circuit 34a, the second latch circuit 34b, and the incidence time calculation circuit 48. The configuration of the other parts of the detection circuit is not limited to that shown in FIG. 11.

In the exemplary detection circuit of a PET apparatus shown in FIG. 11, the number of lines between the substrates 42 and 43 is reduced to two third by using the encoder 44 and the decoder 45.

A $V_1$ detection signal $C_1$, a $V_2$ detection signal $C_2$, and a calculation request signal $C_3$ are output from the first comparator 33a, the second comparator 33b, and the third comparator 33c to the encoder 44, the decoder 45 outputs the $V_1$ detection signal $C_1$, the $V_2$ detection signal $C_2$, and the calculation request signal $C_3$ to the first latch circuit 34a, the second latch circuit 34b, and the incidence time calculation circuit 48, respectively.

Components other than the encoder 44, the decoder 45, and the lines between them in the exemplary detection circuit of a PET apparatus shown in FIG. 11 are substantially the same as those of the detection circuit 40 of the PET apparatus 10 shown in FIG. 8 and have substantially the same functions. Therefore, only the operation of the encoder 44 and the decoder 45 is described below.

Figure 12A:
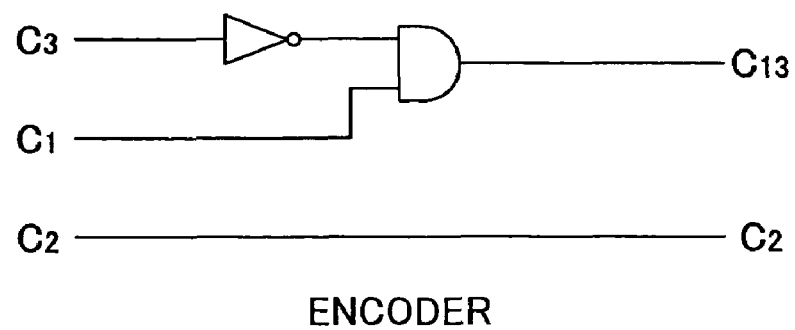
FIG. 12A is a drawing illustrating an encoder.
Figure 12B:
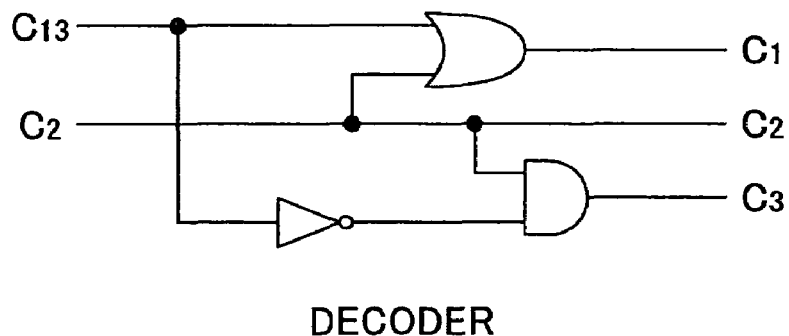
FIG. 12B is a drawing illustrating a decoder.

FIG. 12A is a drawing illustrating the encoder 44 and FIG. 12B is a drawing illustrating the decoder 45.

In the encoder 44 shown in FIG. 12A, the $V_2$ detection signal $C_2$ is output without change, but the following logical operation is performed on the $V_1$ detection signal $C_1$, and the calculation request signal $C_3$ and an output $C_{13}$ is output:

$$\text{output } C_{13} = \overline{C_3} \text{ AND } C_1 \quad (3)$$

In the decoder 45 shown in FIG. 12B, the $V_2$ detection signal $C_2$ is output without change, but the following logical operations are performed on the output $C_{13}$, and the $V_1$ detection signal $C_1$ and the calculation request signal $C_3$ are output.

$$V_1 \text{ detection signal } C_1 = C_{13} \text{ OR } C_2 \quad (4)$$

$$\text{calculation request signal } \overline{C_3} = C_{13} \text{ AND } C_2 \quad (5)$$

Figure 13:
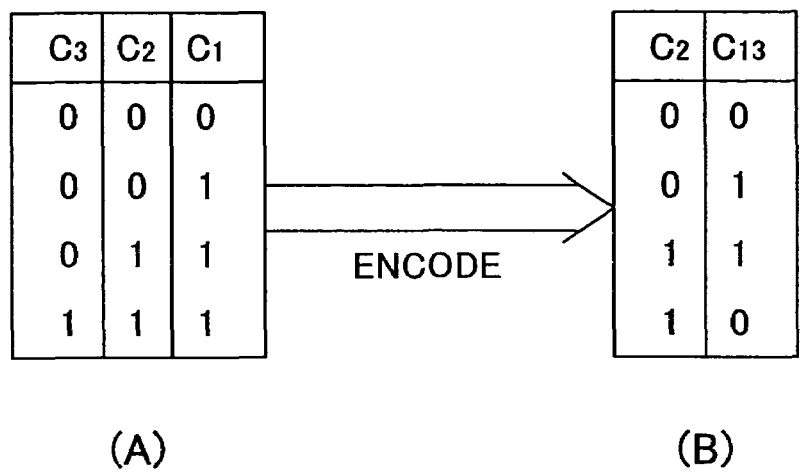
FIG. 13 is a drawing showing tables used to describe operation of an encoder.

The operation of the encoder 44 and the decoder 45 are described below in more detail using figures shown in FIG. 13. The $V_1$ detection signal $C_1$, the $V_2$ detection signal $C_2$, and the calculation request signal $C_3$ are output from the first comparator 33a, the second comparator 33b, and the third comparator 33c.

The first comparator 33a, the second comparator 33b, and the third comparator 33c compare a detected signal with the first threshold voltage $V_1$, the second threshold voltage $V_2$, and the third threshold voltage $V_3$, respectively. When the detected signal matches the threshold voltages, the first comparator 33a, the second comparator 33b, and the third comparator 33c output the $V_1$ detection signal $C_1$, the $V_2$ detection signal $C_2$, and the calculation request signal $C_3$, respectively.

The relationships between the first threshold voltage $V_1$, the second threshold voltage $V_2$, and the third threshold voltage $V_3$ can be expressed as follows:

$$\text{first threshold voltage } V_1 < \text{second threshold voltage } V_2 < \text{third threshold voltage } V_3 \quad (6)$$

The $V_2$ detection signal $C_2$ is 1 only when the $V_1$ detection signal $C_1$ is 1, and the calculation request signal $C_3$ is 1 only when the $V_2$ detection signal $C_2$ is 1.

Therefore, the following four combinations of the values of the $V_1$ detection signal $C_1$, the $V_2$ detection signal $C_2$, and the calculation request signal $C_3$ are possible (also shown in FIG. 13(A)):

$$(C_3, C_2, C_1) = (0, 0, 0) \quad (7)$$

$$(0, 0, 1)$$

$$(0, 1, 1)$$

$$(1, 1, 1)$$

The above combinations of values are encoded by the encoder 44 into the following combination of values (C2, C13) (also shown in FIG. 13B):

$$(C_2, C_{13}) = (0, 0) \quad (8)$$
$$(0, 1)$$
$$(1, 1)$$
$$(1, 0)$$

Figure 14:
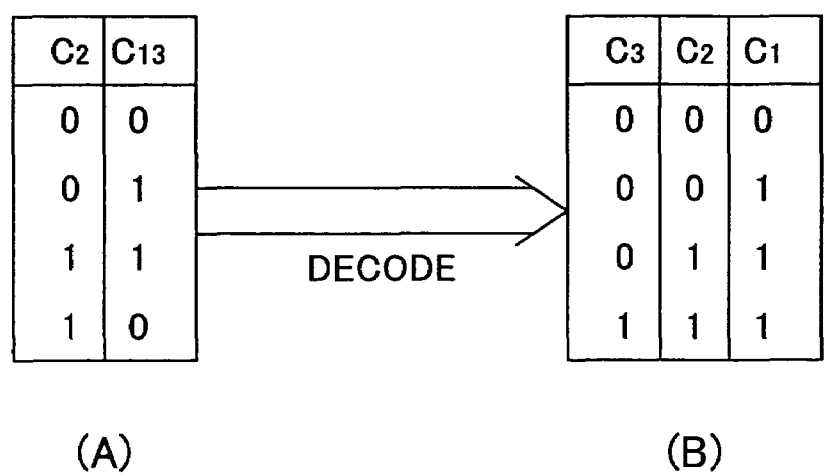
FIG. 14 is a drawing showing tables used to describe operation of a decoder.

The decoder 45 decodes the encoded values ($C_2$, $C_{13}$) into values ($C_3$, $C_2$, $C_1$) as shown in FIG. 14.

As shown in FIG. 13(A) and FIG. 14(B), the decoder 45 decodes the encoded signals into the original signals.

The encoder 44 and the decoder 45 make it possible to connect the substrates 42 and 43 with two lines instead of three lines.

The detector 21 of the detector block 12 shown in FIG. 11 is essentially the same as shown in FIG. 4.

As described earlier, the number of detectors in the detector block 12 is not limited. When, for example, 32 detectors are provided, 96 (3×32) lines are necessary to connect the substrate 42 and the substrate 43 without using the encoder 44 and the decoder 45. However, when the encoder 44 and the decoder 45 are provided, the number of lines can be reduced to 64 (2×32).

Since the lines cannot be connected directly onto the substrate, they are connected by using connectors. Even a narrowest connector currently available has a width of about 0.2 mm. When 96 connectors are provided, the combined width reaches 19.2 mm. Also, spaces are needed on both sides of each of the connectors to install them. Therefore, in practice, 96 connectors occupy a space having a width of more than 20 mm.

The width of a crystalline substrate affects its sensitivity. A narrower substrate provides better results. However, because of the widths of connectors, it has been difficult to reduce the width of a substrate.

The third embodiment of the present invention makes it possible to connect the substrates 42 and 43 with a fewer number of lines and thereby makes it possible to obviate the above mentioned problem.

As described above, the third embodiment of the present invention makes it possible to reduce the number of lines (the number of connectors), thereby making it possible to reduce the size of a crystalline substrate and to reduce the time $t_0$ connect the lines.

According to an embodiment of the present invention, a detection circuit determines a first crossing time at which the pulse height of a detected signal becomes substantially equal to the first threshold value and a second crossing time at which the pulse height of the detected signal becomes substantially equal to the second threshold value; and calculates a starting time or an incidence time of the detected signal based on the first crossing time and the second crossing time. Such a mechanism makes it possible to implement a detection circuit without using a delay circuit formed by connecting many operational amplifiers and to implement a detection circuit with a simple configuration including two measurement units for determining the pulse heights of a detected signal.

Forming a detection circuit on a semiconductor chip according to an embodiment of the present invention eliminates the need to rebuild the detection circuit to change the delay time of its delay circuit, thereby reducing the production costs and production time.

According to an embodiment of the present invention, the starting time is calculated based on the first crossing time, the second crossing time, the first threshold value, and the second threshold value. Also, the starting time may be calculated by linear regression. Since the pulse height of the waveform of a detected signal can be approximated by a linear function of a crossing time, a starting time can be calculated accurately by linear regression.

According to an embodiment of the present invention, the detection unit further includes a comparison unit that compares the pulse height of the detected signal with a third threshold value that is greater than the second threshold value and, when the pulse height becomes substantially equal to the third threshold value, outputs a signal requesting the incidence time calculation unit to calculate the starting time. This mechanism makes it possible to invalidate a detected signal the pulse height of which does not reach the third threshold value and thereby to improve the reliability of examination using a PET apparatus.

Embodiments of the present invention make it possible to implement a detection circuit with a simple configuration without using a delay circuit as in a conventional detection circuit as shown in FIG. 1.

The present invention is not limited to the specifically disclosed embodiments, and variations and modifications may be made without departing from the scope of the present invention.

For example, although a PET apparatus is taken as an example to describe the first and second embodiments, the present invention may be applied to a single photon emission computed tomography (SPECT) apparatus. There are several types of SPECT apparatuses including a single-detector SPECT apparatus having one detector block and a dual-detector SPECT apparatus having two detector blocks that are arranged so that their gamma ray incident planes are positioned at right angles to each other or two detector blocks that are arranged to face each other. The present invention can be applied to either of the above types.

In the third embodiment, three signals are input to the encoder 44 and the encoder 44 outputs two signals. However, the input signals are not limited to three and the output signals are not limited to two.

Further, although the $V_1$ detection signal $C_1$, the $V_2$ detection signal $C_2$, and the calculation request signal $C_3$ are converted into four two bit patterns as shown in formula (8) in the third embodiment, other conversion methods may also be used.

The present application is based on Japanese Patent Application No. 2005-069926 filed on Mar. 11, 2005, and Japanese Patent Application No. 2005-140125 filed on May 12, 2005, the entire contents of which are hereby incorporated herein by reference.

What is claimed is:

1. An apparatus for radiographic examination, comprising:
   a detection unit which comprises
      a detector configured to detect a gamma ray emitted from a radioactive isotope in an object and to output a detected signal,
      a first measurement unit configured to determine a first crossing time at which a pulse height of the detected signal becomes substantially equal to a first threshold value,
      a second measurement unit configured to determine a second crossing time at which the pulse height of the detected signal becomes substantially equal to a second threshold value that is greater than the first threshold value, and an incidence time calculation unit configured to calculate a starting time of the detected signal based on the first crossing time and the second crossing time, which the starting time indicates when a waveform of the detected signal has started to rise and is used as an incidence time indicating when the gamma ray has entered the detector, and to output detection data including the incidence time; and an information processing unit configured to determine distribution of radioactive isotopes in the object based on multiple sets of said detection data that are valid according to the incidence time.

2. The apparatus for radiographic examination as claimed in claim 1, wherein the starting time is calculated based on the first crossing time, the second crossing time, the first threshold value, and the second threshold value.

3. The apparatus for radiographic examination as claimed in claim 2, wherein the starting time is calculated by linear regression.

4. The apparatus for radiographic examination as claimed in claim 1, wherein the detection unit further comprises a first timer that, when a specified amount of time passes after the first crossing time is determined and before the second crossing time is determined, is configured to output a signal requesting the incidence time calculation unit to discard the first crossing time.

5. The apparatus for radiographic examination as claimed in claim 1, wherein the detection unit further comprises a comparison unit configured to compare the pulse height of the detected signal with a third threshold value that is greater than the second threshold value and, when the pulse height becomes substantially equal to the third threshold value, to output a signal requesting the incidence time calculation unit to calculate the starting time.

6. The apparatus for radiographic examination as claimed in claim 5, wherein the detection unit further comprises a second timer that, when a specified amount of time passes after the second crossing time is determined and before the pulse height of the detected signal becomes substantially equal to the third threshold value, is configured to output a signal requesting the incidence time calculation unit to discard the first crossing time and the second crossing time.

7. The apparatus for radiographic examination as claimed in claim 1, wherein the detection unit further includes a waveform shaping unit between the detector and the first measurement unit which waveform shaping unit is configured to shape the waveform of the detected signal and includes a first-order low-pass filter, a second-order low-pass filter, or a third-order low-pass filter.

8. The apparatus for radiographic examination as claimed in claim 1, wherein the first threshold value is set to a value corresponding to a gamma ray energy level of between 8 keV and 100 keV.

9. The apparatus for radiographic examination as claimed in claim 1, wherein
the detector includes a semiconductor crystal, a first electrode substantially covering one side of the semiconductor crystal, and stripe-shaped second electrodes formed on the other side of the semiconductor crystal; and
the detected signal is output from one of the second electrodes.

10. A radiation detection circuit for obtaining an incidence time indicating when a gamma ray has entered a detector, comprising:
a first measurement circuit configured to determine a first crossing time at which a pulse height of a detected signal output from the detector becomes substantially equal to a first threshold value;
a second measurement circuit configured to determine a second crossing time at which the pulse height of the detected signal becomes substantially equal to a second threshold value that is greater than the first threshold value; and
an incidence time calculation circuit configured to calculate a starting time of the detected signal based on the first crossing time and the second crossing time, which the starting time indicates when a waveform of the detected signal has started to rise and is used as the incidence time.

11. The radiation detection circuit as claimed in claim 10, further comprising:
a first comparison circuit configured to compare the pulse height of the detected signal with a third threshold value that is greater than the second threshold value and, when the pulse height becomes substantially equal to the third threshold value, to output a signal requesting the incidence time calculation circuit to calculate the starting time.

12. The radiation detection circuit as claimed in claim 11, further comprising:
a second comparison circuit that, when the pulse height of the detected signal becomes substantially equal to the first threshold value, is configured to send a signal to the first measurement circuit;
a third comparison circuit that, when the pulse height of the detected signal becomes substantially equal to the second threshold value, is configured to send a signal to the second measurement circuit;
an encoder that is configured to encode the signals from the first comparison circuit, the second comparison circuit, and the third comparison circuit; and
a decoder that is configured to decode the encoded signals.

13. The radiation detection circuit as claimed in claim 12, wherein
the radiation detection circuit is formed on a first substrate and a second substrate;
the first comparison circuit, the second comparison circuit, the third comparison circuit, and the encoder are formed on the first substrate; and
the first measurement circuit, the second measurement circuit, the incidence time calculation circuit, and the decoder are formed on the second substrate.

* * * * *